(12) United States Patent
Chen et al.

(10) Patent No.: US 8,582,857 B2
(45) Date of Patent: Nov. 12, 2013

(54) DUAL-ENERGY MATERIAL IDENTIFICATION METHOD AND APPARATUS WITH UNDERSAMPLING

(75) Inventors: Zhiqiang Chen, Beijing (CN); Li Zhang, Beijing (CN); Yuanyuan Liu, Beijing (CN); Yuxiang Xing, Beijing (CN); Ziran Zhao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 80 days.

(21) Appl. No.: 13/322,243

(22) PCT Filed: Dec. 30, 2009

(86) PCT No.: PCT/CN2009/076295
§ 371 (c)(1),
(2), (4) Date: Feb. 21, 2012

(87) PCT Pub. No.: WO2010/135900
PCT Pub. Date: Dec. 2, 2010

(65) Prior Publication Data
US 2012/0148133 A1    Jun. 14, 2012

(30) Foreign Application Priority Data

May 27, 2009  (CN) .......................... 2009 1 0085925

(51) Int. Cl.
*G06K 9/00* (2006.01)
*A61B 6/00* (2006.01)
*A61B 5/05* (2006.01)

(52) U.S. Cl.
USPC ............................. 382/131; 378/4; 600/425

(58) Field of Classification Search
USPC ......... 382/128, 129, 130, 131, 132, 133, 134, 382/164; 378/4, 5, 8, 9, 21–27, 57, 62, 68, 378/88, 901; 600/407, 410, 425, 427
See application file for complete search history.

(56) References Cited

U.S. PATENT DOCUMENTS 7,190,757 B2 *  3/2007  Ying et al. ......................... 378/5
7,197,172 B1 *  3/2007  Naidu et al. ................... 382/131

FOREIGN PATENT DOCUMENTS

| CN | 101237819 | 8/2008 |
|----|-----------|--------|
| CN | 101433464 | 5/2009 |

OTHER PUBLICATIONS

International Search Report from Application No. PCT/CN2009/076295, dated Apr. 8, 2010, 4 pgs.

(Continued)

*Primary Examiner* — Abolfazl Tabatabai
(74) *Attorney, Agent, or Firm* — Westman, Champlin & Koehler, P.A.

(57) ABSTRACT

A dual-energy material identification method and system with under-sampling is disclosed. A CT image of the object is obtained by using the CT image reconstruction method, while the dual-energy projections are under-sampled to obtain a few samples. Photoelectric coefficient integral and Compton coefficient integral are computed from these dual-energy projection data. The CT image is segmented into regions with image processing technique, and the regions are labeled. The length by which a few dual-energy rays crosses each labeled region is computed, and an equation system is established with dual-energy preprocessing dual-effect decomposition reconstruction method to compute Photoelectric coefficient and Compton coefficient, and then atomic number and electron density of material in each region are computed. The material of the object can be identified with the atomic number.

14 Claims, 9 Drawing Sheets

(56) References Cited

OTHER PUBLICATIONS

Written Opinion from Application No. PCT/CN2009/076295, dated Apr. 8, 2010, 5 pgs.

"A Volumetric Object Detection Framework with Dual-Energy CT," Bi et al., 2008 IEEE Nuclear Science Symposium Conference Record, N02-457, pp. 1289-1291, 3 total pages.

"Improved Single-Pass Split-Merge Image Segmentation in the Application of the Dual Energy CT Reconstruction Method with Reduced Data," Liu et al., © 1994-2011 China Academic Journal Electronic Publishing House, http://www.cnki.net, 5 total pages (abstract).

* cited by examiner

DUAL-ENERGY MATERIAL IDENTIFICATION METHOD AND APPARATUS WITH UNDERSAMPLING

CROSS-REFERENCE TO RELATED APPLICATION

This Application is a Section 371 National Stage Application of International Application No, PCT/CN2009/076295, filed 30 Dec. 2009 and published as WO 2010/135900 on Dec. 2, 2010, in Chinese, the contents of which are hereby incorporated by reference in their entirety.

TECHNICAL FIELD

The present invention relates to radiography technology, in particular to dual-energy material identification methods and apparatuses with under-sampling, which can reduce radiation dose and system cost and increase scanning speed.

BACKGROUND

Recently, dual-energy CT imaging technology has been playing an importance role in various fields like security inspection, lossless detection and medical treatment, as it can achieve optimal detection accuracy and enable efficient object reconstruction and material identification.

Figure 1:
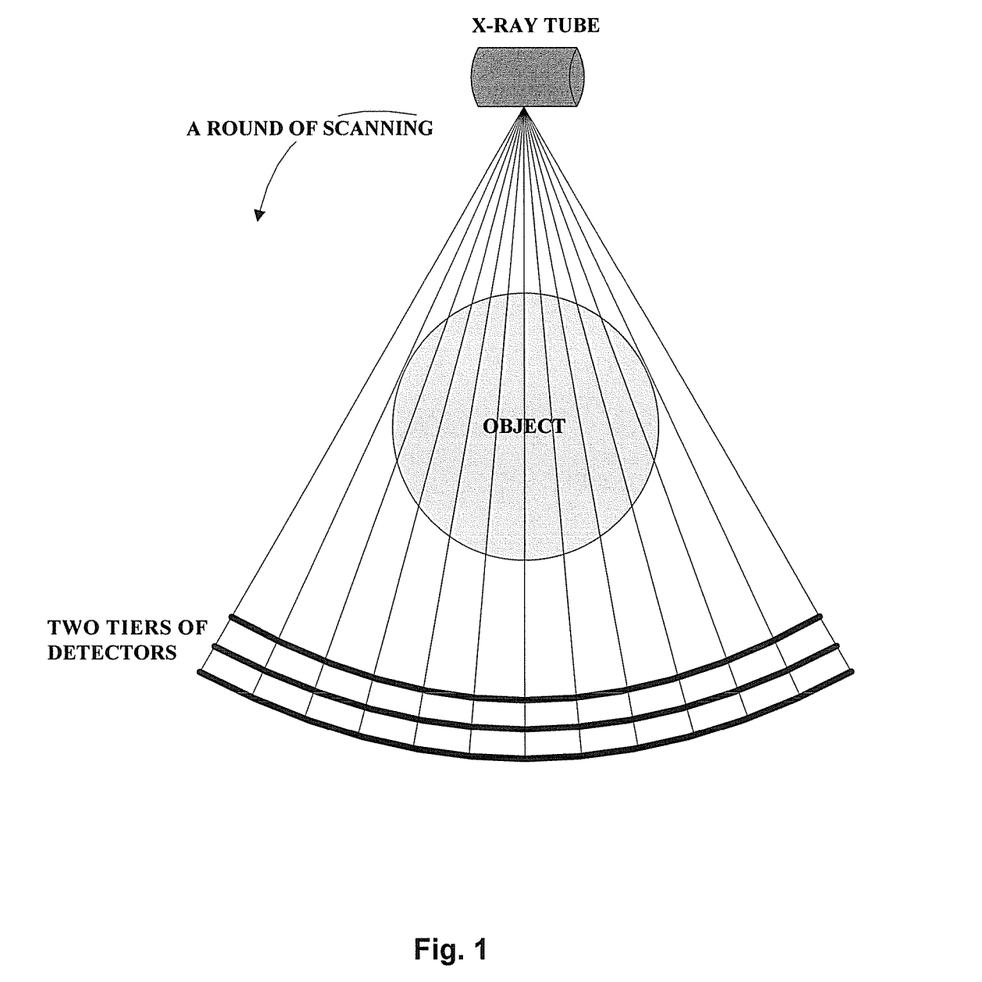
FIG. 1 is a schematic planar diagram showing a circular trajectory scanning of a pseudo dual-energy CT imaging system.

There are currently two primary implementations for a dual-energy CT imaging method. One of the implementations is a pseudo dual-energy system which performs dual-energy imaging with specifically designed double-tiered detectors, as shown in FIG. 1. In the system of FIG. 1, when scanning is performed, rays penetrate through an object and first arrive at the first tier of low-energy detectors. Then, the rays transmit filtering sheets and finally arrive at the second tier of high-energy detectors. At the same time, respective pixels of two resultant transmission images are automatically in correspondence with identical ray paths.

Figure 2A:
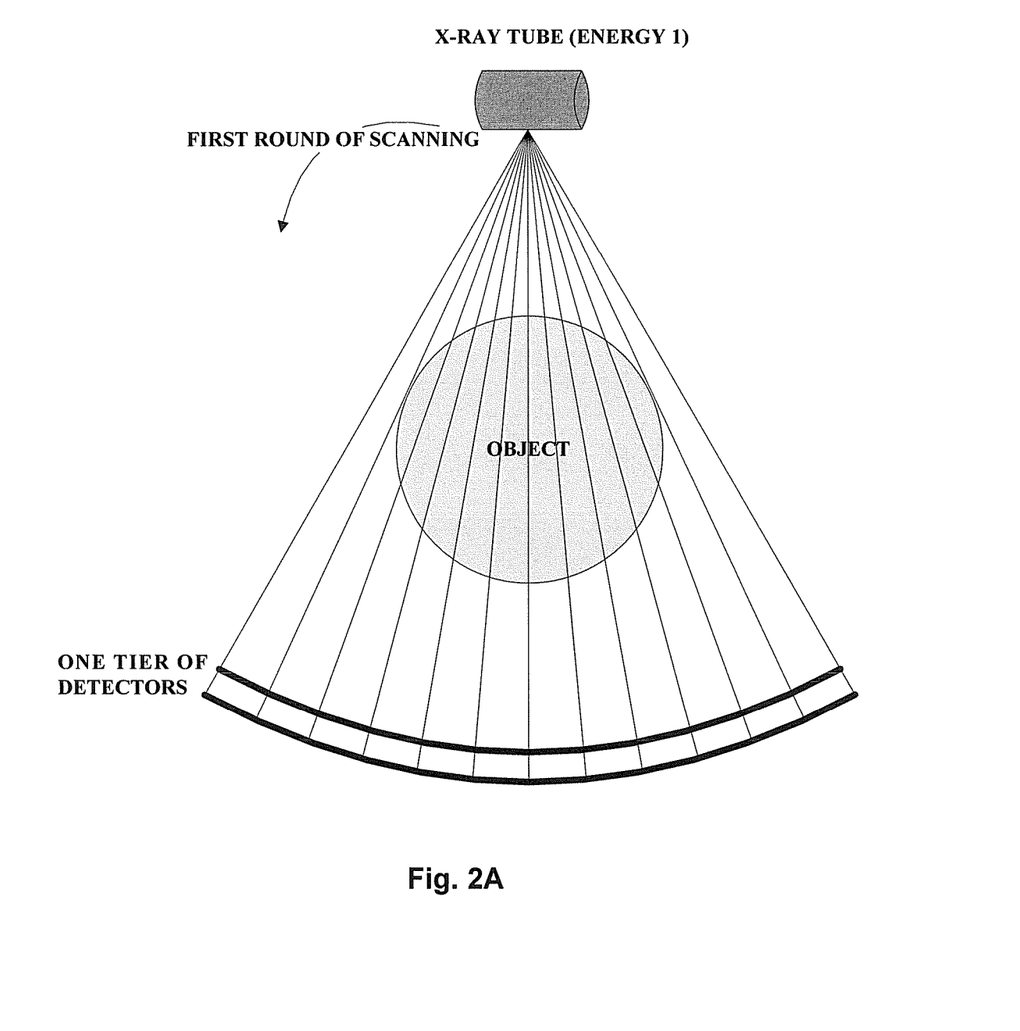
FIGS. 2A and 2B are schematic planar diagrams showing a circular trajectory scanning of a real dual-energy CT imaging system.
Figure 2B:
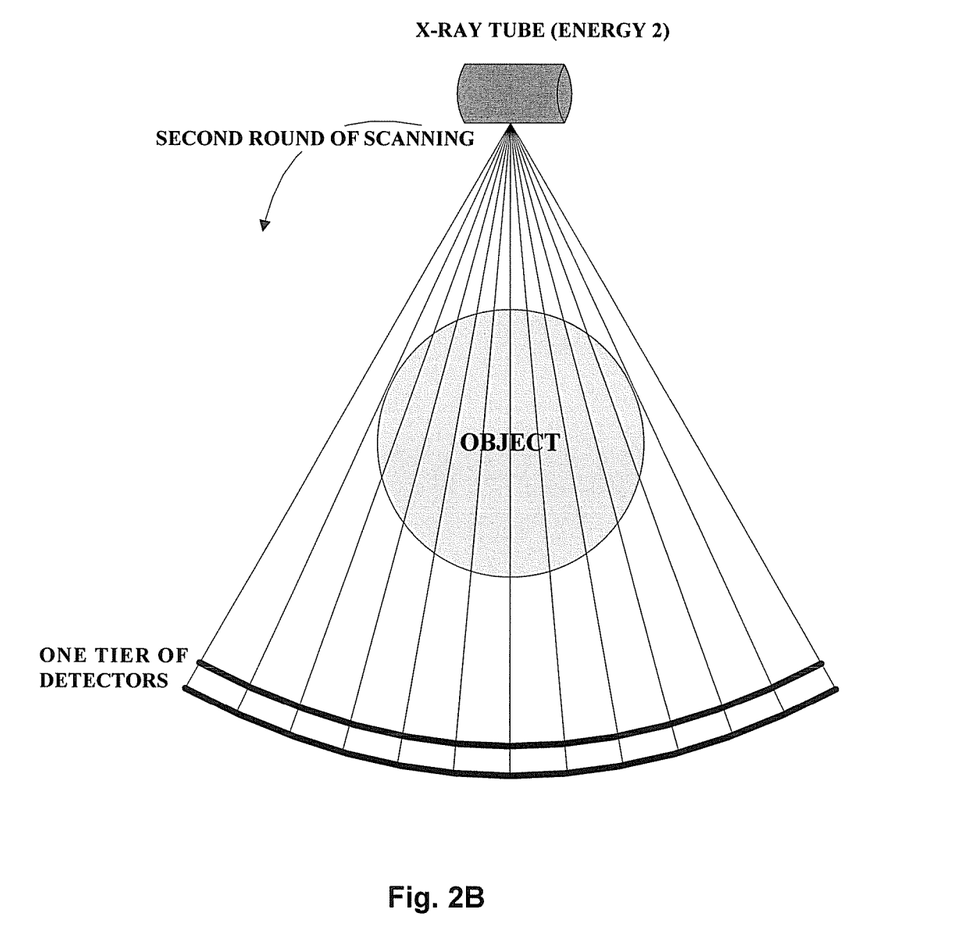

The other implementation is a real dual-energy system which performs circular scanning on an object using ray sources of different energy levels, as shown in FIGS. 2A and 2B. During the first round of scanning shown in FIG. 2A, the object is scanned with rays at a first energy level. Then, the rays are switched from the first energy level to the second energy level. During the second round of scanning shown in FIG. 2B, the object is scanned with rays at the second energy level. The method shown in FIGS. 2A and 2B requires radiation dose and scanning time two times more than a single-scanning method. Image matching is also required between transmission images of low and high energy levels to ensure pixels of the two images at the same coordinate correspond to the same ray path.

From the perspective of engineering realization, however, the system of the above first implementation is expensive and thus hard for wide application, due to the need for simultaneous collecting by two tiers of detectors. The second system has strict requirement on matching of transmission images between low and high energy levels. Further, the second system takes longer time due to a slow scanning speed and large scanning dose for the object due to the additional second round of scanning. These shortcomings adversely affect the popularization of dual-energy CT imaging technology.

SUMMARY

It is an object of the present invention to provide dual-energy material identification method and system with under-sampling, to address the difficulties such as the high cost, large dose and slow speed scanning in the existing systems for reconstructing an object and identifying materials with dual-energy CT imaging technology. Methods and systems according to embodiments of the present invention can be applied to various fields including security inspection, lossless detection and medical treatment.

In one aspect of the present invention, a dual-energy material identification method with under-sampling is provided comprising:

CT scanning an object under inspection with ray beams at a first energy level to obtain projection data at respective angles at the first energy level, and reconstructing a CT image of the object;

CT scanning the object with ray beams at a second energy level to obtain projection data at a part of the respective angles at the second energy level;

combining the projection data at the first and second energy levels to obtain dual-energy under-sampled data at the part of the respective angles;

acquiring a photoelectric coefficient integral value and a Compton coefficient integral value from the dual-energy under-sampled data;

segmenting the CT image of the object into a plurality of regions and computing a length by which the dual-energy rays cross each of the regions;

computing the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

computing at least atomic number of material in each of the regions based on the photoelectric coefficient and the Compton coefficient; and identifying the material of the object based on at least the atomic number.

In another aspect of the present invention, a dual-energy material identification system with under-sampling is provided comprising:

a ray generating device configured to generate ray beams at a first energy level and ray beams at a second energy level, the ray beams being intended to penetrate through an object under inspection;

a mechanic rotation control section comprising a rotation device and a control system and configured to perform a rotatory scanning on the object;

a data collecting subsystem comprising one tier of array of detectors and configured to acquire transmission projection data for the ray beams penetrating through the objection;

a master control and data processing computer configured to control the ray generating device, the mechanic rotation control section and the data collecting subsystem to CT scan the object with ray beams at a first energy level to obtain projection data at respective angles at the first energy level, reconstruct a CT image of the object, and CT scan the object with ray beams at a second energy level to obtain projection data at a part of the respective angles at the second energy level;

wherein the master control and data processing computer is configured to:

combine the projection data at the first and second energy levels to obtain dual-energy under-sampled data at the part of the respective angles;

acquire a photoelectric coefficient integral value and a Compton coefficient integral value from the dual-energy under-sampled data;

segment the CT image of the object into a plurality of regions, and compute a length by which the dual-energy rays cross each of the regions;

compute the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

compute at least atomic number of material in each of the regions based on the photoelectric coefficient and the Compton coefficient; and identify the material of the object based on at least the atomic number.

Compared with the traditional pseudo dual-energy system having two tiers of detectors, the CT-imaging-based dual-energy material identification method and system with under-sampling can reduce the detectors and cost, and thus make it possible for the dual-energy material identification imaging system to be widely applied in security inspection. Compared with the real dual-energy system, the methods and systems of the present invention can decrease rounds of rotation and thus achieve faster and small-dose dual-energy material identification and imaging. This contributes to speedup of security inspection and reduction of radiation dose received by a patient during medical treatment.

The method and system according to embodiments of the present invention can effectively solve several difficulties in dual-energy material identification imaging, with CT image being used as a priori. It can realize a fast scanning with low cost and dose, and is highly potential for commercial uses.

BRIEF DESCRIPTION OF THE DRAWINGS

The above features and advantages of the present invention will be more apparent from the following detailed description in conjunction with accompanying drawings in which.

DETAILED DESCRIPTION OF THE PREFERRED EMBODIMENTS

Hereafter, preferred embodiments of the present invention will be elaborated with reference to the figures. Throughout the figures, the same reference sign denotes identical or similar component. For clarity and conciseness, detailed description of any known function and structure herein will be omitted, otherwise the subject matter of the present invention may be obscured.

Figure 3A:
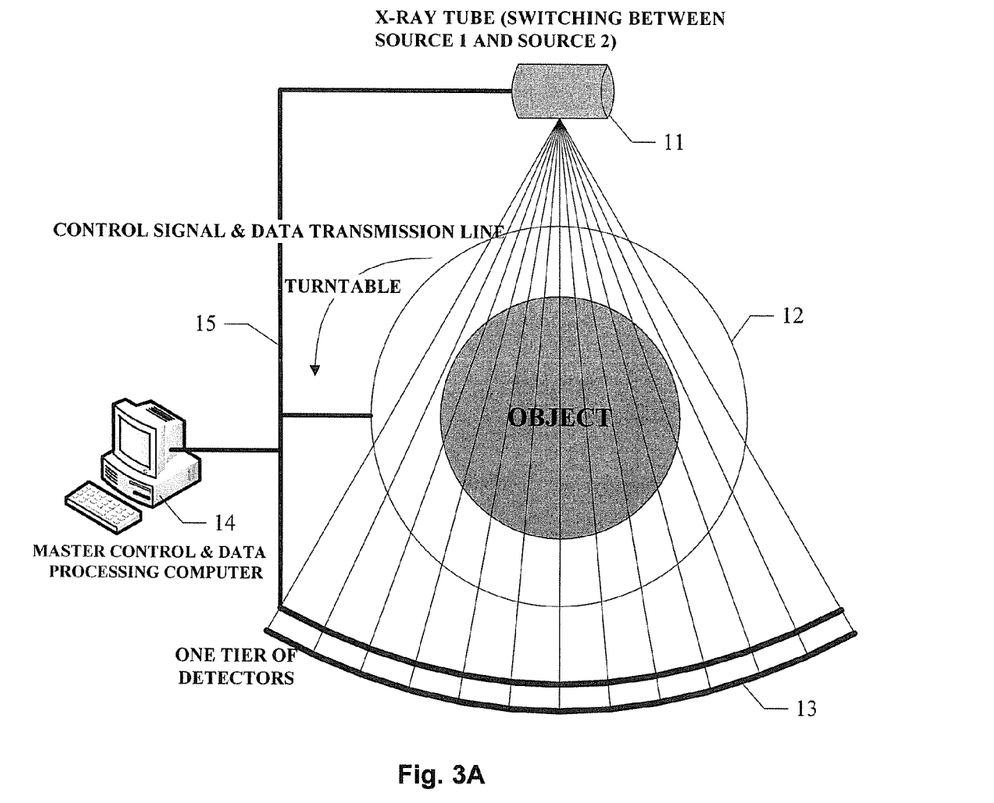
FIG. 3A is a schematic block diagram of an improved real dual-energy detection system for material identification and imaging according to an embodiment of the present invention.
Figure 5A:
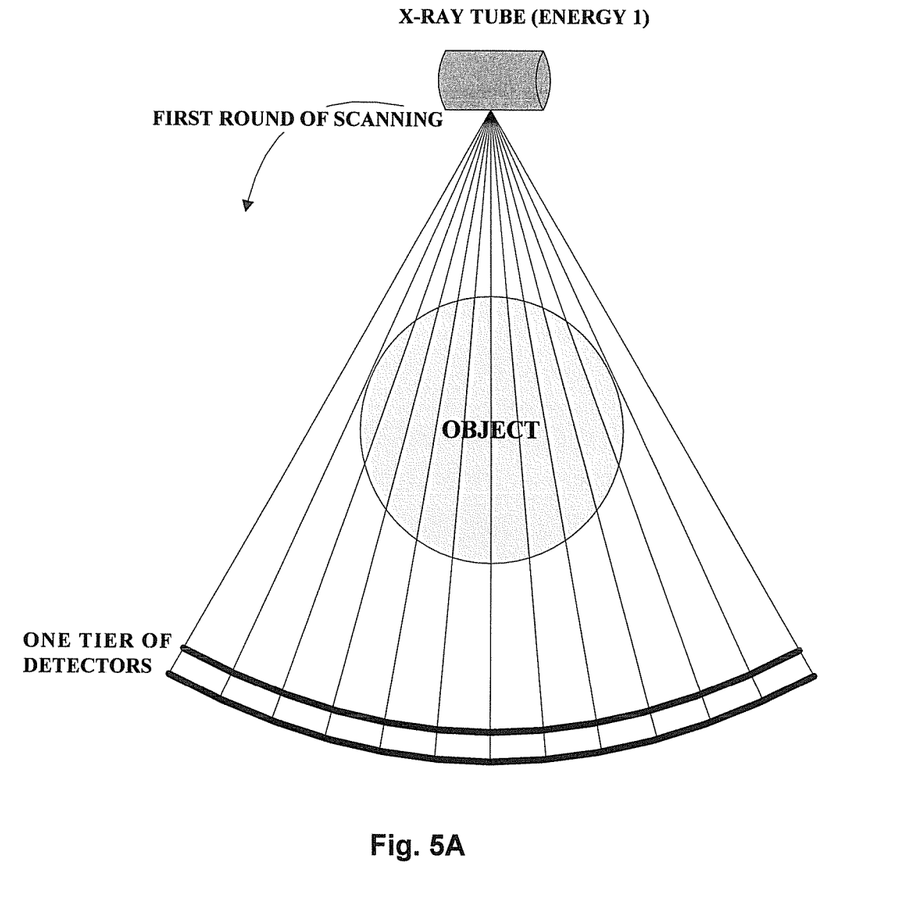
FIGS. 5A and 5B are schematic planar diagrams showing a circular trajectory scanning of an improved real dual-energy detection system for material identification and imaging according to an embodiment of the present invention.
Figure 5B:
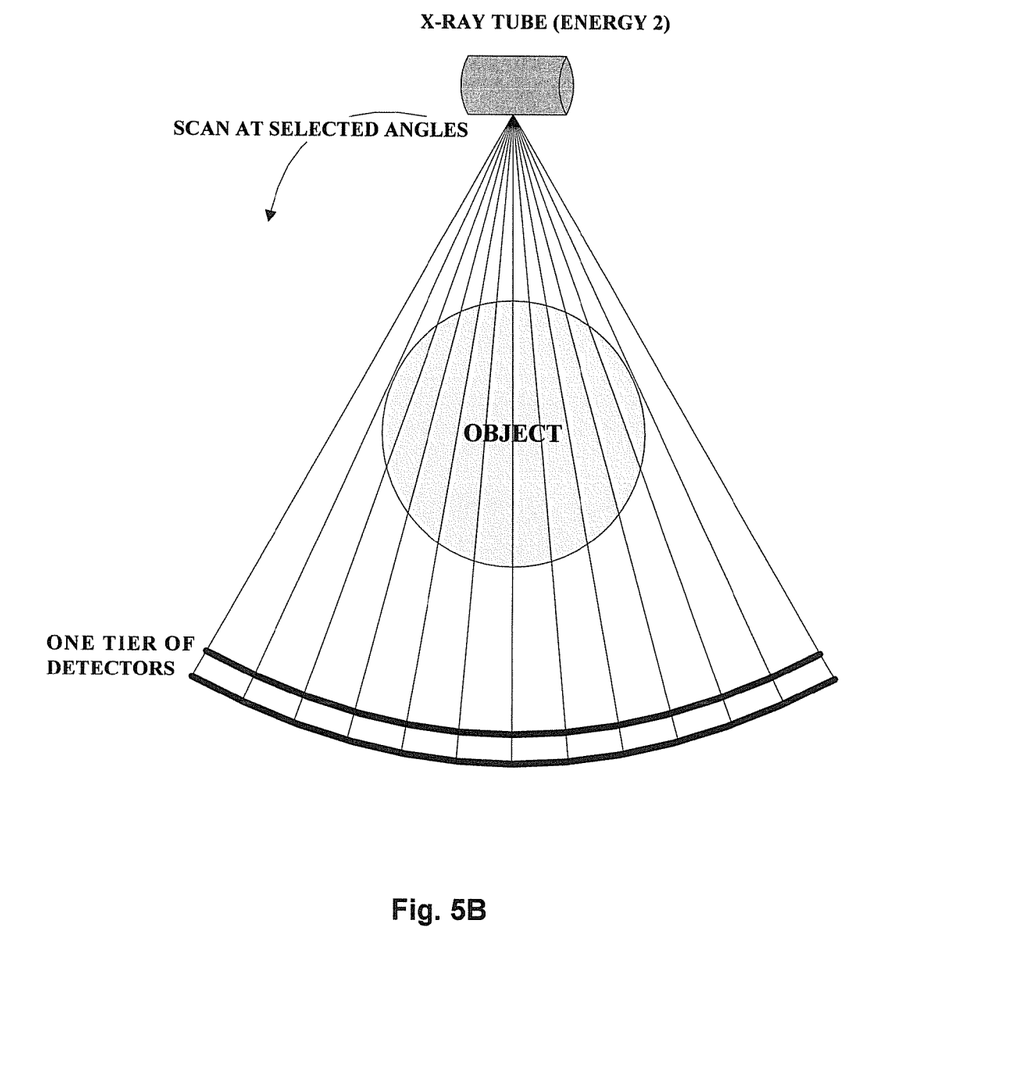

The system according to an embodiment of the present invention is an improved real dual-energy, circular-trajectory detection system for material identification, imaging and detection, which can implement a CT-imaging-based material identification method with under-sampling of dual-energy projections. As shown in FIG. 3A, the system employs circular-trajectory fan-beam scanning by means of a ray source and one tier of detectors. As shown in FIGS. 5A and 5B, a CT image reconstructed from a first round of circular-trajectory scanning is used to obtain information about the object's structure or the shape of contents contained in the object. Then, a few samples of dual-energy projections are obtained from information about projections at one or more angles of a second round of scanning. In this way, it is possible to implement dual-energy material identification imaging with higher speed and smaller dose. As shown in FIG. 5A, during the first round of scanning, low-energy rays are used to perform a normal scanning for a complete 360° sampling, and then a CT image is reconstructed. In the second round, selective scanning with high-energy rays is performed to obtain high-energy projection data over a part of the angles over 360 degrees.

As shown in FIG. 3A, the system according to the present embodiment may include a ray generating device 11, a mechanic rotation control section 12, a data collecting subsystem 13, and a master control and data processing computer 14.

The ray generating device 11 includes an X-ray accelerator, an X-ray machine, or radioactive isotope, and respective auxiliary equipments.

The mechanic rotation control section 12 includes a rotation device and a control system configured to rotate an object (or source and detector). The movement of the object is relative to the movement of the source and detector, and thus the two movements are equivalent to each other. In medical area, it is usually rotating both of source and detectors instead of a patient, because the patient has difficulty to move. In the present embodiment, the object is rotated.

The data collecting subsystem 13 primarily includes one tier of array of detectors (generally, the detectors are arranged equidistantly, while they can be arranged equiangularly) for acquiring transmission projection data of the rays. The subsystem 13 further includes projection data sensing circuits, logic control units and the like over the detectors. The detectors may be solid, gaseous or semiconductor detectors.

During the process of data collection, it is required that sampling intervals are uniformly distributed on the time axis, the object moves at a uniform speed, and all of the detectors in the array collect data in a synchronized manner.

The master control and data processing computer 14 sends and receives signals via a control signal and data transmission line 15, and conducts a master control over the operations of the CT system, including mechanic rotation, electrical control, safety interlocking control and the like. The computer 14 processes the projection data acquired by the data collecting subsystem 13. The computer 14 reconstructs a tomogram image of the object from the projection data collected in the first round, segments the image into several regions, and labels these regions. Then, by utilizing a few samples obtained in the second round of scanning to combine into a few dual-energy projection samples, the computer 14 reconstructs the atomic number and electron density images for materials in the segmented regions for material identification, and displays the images on a display. The computer 14 may be a single Personal Computer (PC) with high performance, or may be a work station or a group of computers.

Figure 3B:
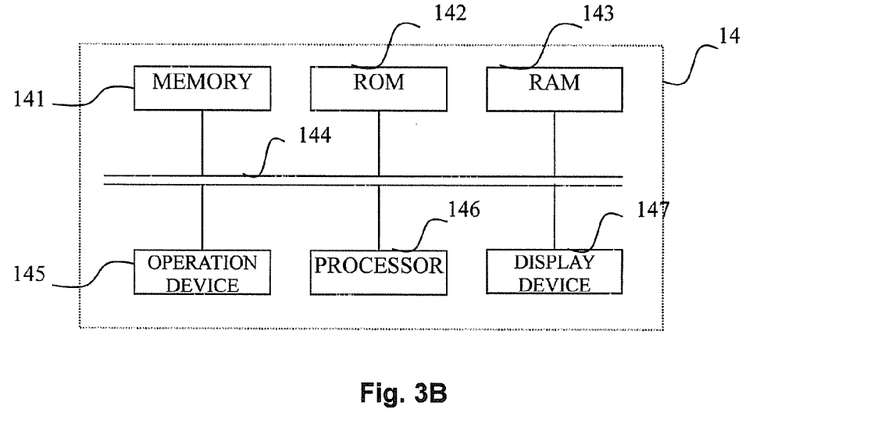
FIG. 3B is a schematic block diagram of a master control and data processing computer shown in FIG. 3A.

FIG. 3B shows a schematic block diagram of the master control and data processing computer 14 in FIG. 3A. In FIG. 3B, the data collected by the data collecting subsystem 13 are stored in a storage device 141. Read Only Memory (ROM) 142 has stored therein configuration information and program for data processing computer. Random Access Memory (RAM) 143 is configured to temporally store various data during the operation of processor 146. The storage device 141 also stores computer program for data processing and a pre-programmed database. The database maintains information about various known objects, a lookup table for photoelectric coefficient integral values and Compton coefficient integral values, a lookup table or a classification graph for atomic numbers, electron densities for materials, and so on. These items of information are used for comparison with the computed (by the processor 146) attributes (such as atomic number, electron density) of materials in respective regions of the object image. Internal bus 144 connects among the storage device 141, ROM 142, RAM 143, input device 145, processor 146 and display device 147.

After an operator inputs an operation command via the input device 145 such as keyboard or mouse, the processor 146 executes computer program for a predetermined data processing algorithm and obtains a result of data processing. Then, the result is displayed on the display device 147, such as LCD display, or directly outputted in a hardcopy form.

Figure 4:
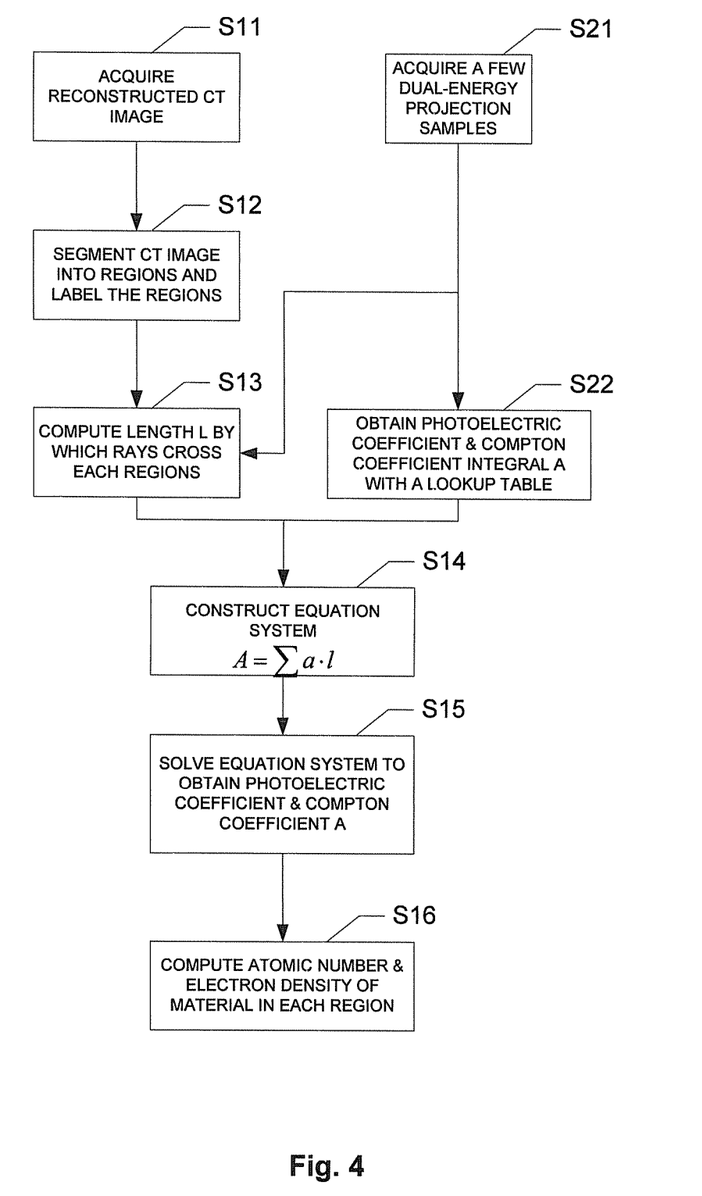
FIG. 4 is a schematic flowchart of a CT-imaging-based material identification method with under-sampled dual-energy projections according to an embodiment of the present invention.

Hereafter, a method according to an embodiment of the present invention will be described with reference to FIG. 4. FIG. 4 shows a schematic flowchart of a CT-imaging-based material identification method with under-sampled dual-energy projections according to an embodiment of the present invention.

At step S11, the master control and data processing computer 14 controls the ray generating device 11, the mechanic rotation control section 12 and the data collecting subsystem 13 to acquire samples of projection data during a first round of scanning with Energy 1 and reconstructs from the samples a CT image of the object, in accordance with the circular-trajectory fan-beam scan and reconstruction method. At step S21, a few samples of projection data are acquired at a single angle or several angles during the second round of scanning with Energy 2, and these samples are combined with the samples acquired during the first round into a few of under-sampled dual-energy projection data. In other words, the projection data of the object are under-sampled during the second round of scanning.

According to an embodiment of the present invention, the number of angles at which the second round of scanning are performed may be only one or more than one. In the case of more than one angles, projection data at these angles preferably have less correlation, for example, less than a predefined threshold value.

Then at step S22, reference may be made to the lookup table maintained in the memory 141 of the computer 14 to find out photoelectric coefficient integral and Compton coefficient integral A corresponding to each pair of higher and lower energy projections. It is understood that any other approach can be used to find out the integral A, while the present embodiment is illustrated with the example of using a lookup table.

Figure 6:
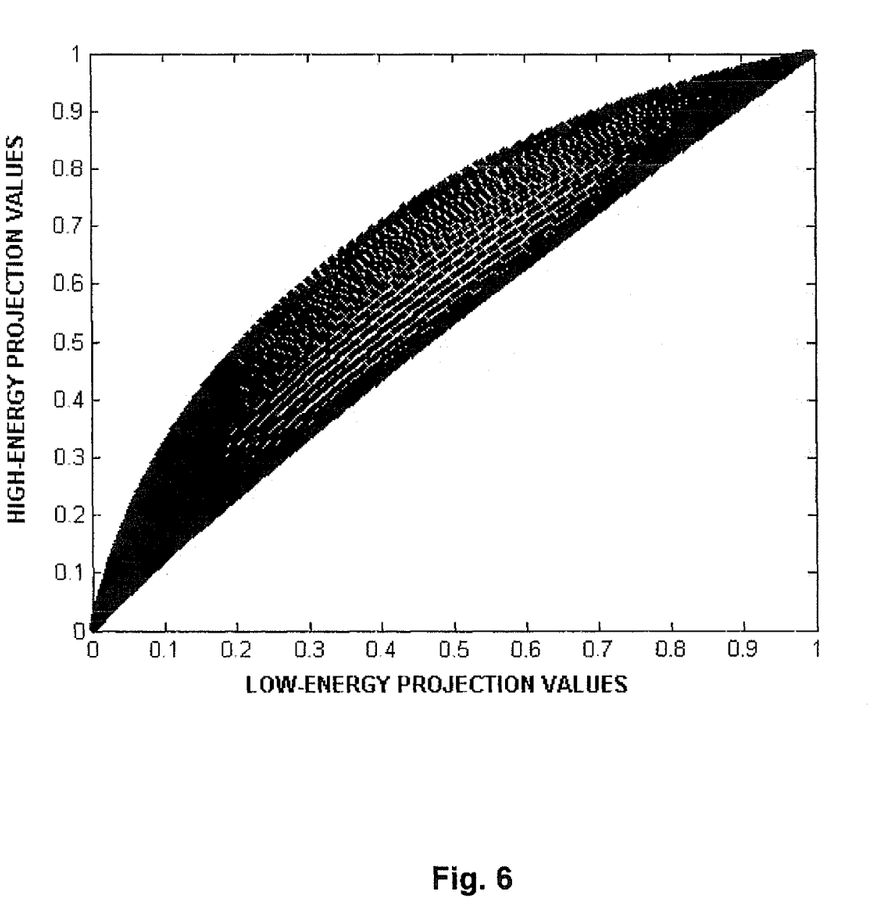
FIG. 6 shows a lookup table of the photoelectric coefficient integral values and the Compton coefficient integral values.

In FIG. 6, the abscissa and ordinate represent projections at lower and higher energy levels, respectively. At each of the coordinates within the table, there is a value for photoelectric coefficient integral and Compton coefficient integral A corresponding to the higher and lower energy projection data. When the higher and lower energy projection data are given, the value for photoelectric coefficient integral and Compton coefficient integral A can be obtained by looking up the table. More details of such lookup table can be found in a document titled "A Volumetric Object Detection Framework with Dual-Energy CT", IEEE NSS/MIC 2008.

At step S12, the master control and data processing computer 14 divides the reconstructed CT images into several individual regions based on the grayscale differences between these regions by using the technique of image segmentation, and labels the divided regions. The technique of image segmentation may be, for example, a modified one-way split-and-merge approach.

Figure 7:
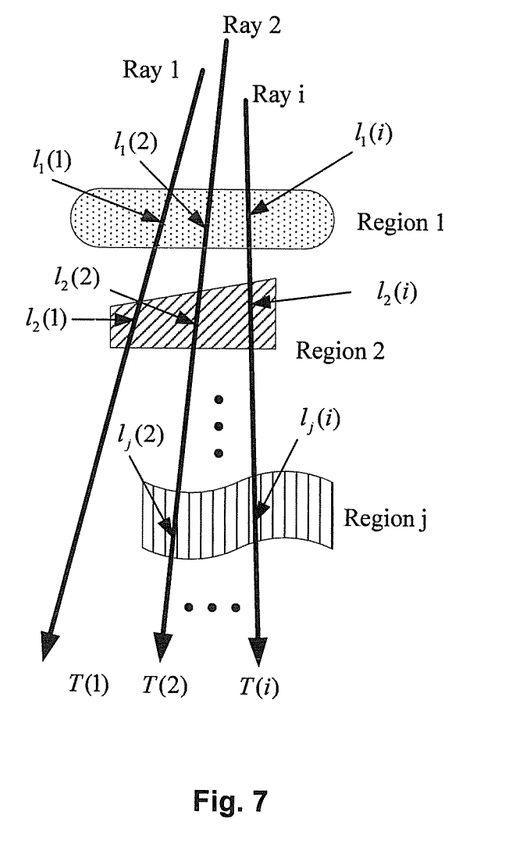
FIG. 7 is a schematic diagram depicting computation of lengths of rays crossing the segmented regions.

In FIG. 7, $l_j(i)$ represents the length by which the ith ray crosses the jth region, and T(i) represents projection data. At step S13, the length $l_j(i)$ by which the ray beams corresponding to the ith set of projection data crosses the jth region is computed on the basis of the samples of dual-energy projections obtained at step S21.

At step S14, by using the dual-energy preprocessing dual-effect decomposition reconstruction method, the master control and data processing computer 14 establishes a equation system A=Σa·l, where a represents Compton coefficient and photoelectric coefficient. It is assumed that M sets of DR dual-energy transmission data are obtained during the second round of scanning, the CT image are segmented into N labeled regions, and $T_H(i)$ and $T_L(i)$ represent the ith sets of high- and low-energy projection data. Then, the dual-effect decomposition is performed on linear attenuation coefficients according to the following formula (1):

$$\mu(E) = a_1 f_{ph}(E) + a_2 f_{KN}(E) \quad (1)$$

Further, the high- and low-energy transparencies are represented by the following formulas (2) and (3):

$$T_H = \int_{E_H} D_H(E) \exp\left(-\int \mu(E) dl\right) dE \quad (2)$$

$$= \int_{E_H} D_H(E) \exp(-A_1 f_{ph}(E) - A_2 f_{KN}(E)) dE$$

$$T_L = \int_{E_L} D_L(E) \exp\left(-\int \mu(E) dl\right) dE \quad (3)$$

$$= \int_{E_L} D_L(E) \exp(-A_1 f_{ph}(E) - A_2 f_{KN}(E)) dE$$

wherein $f_{ph}(E)$ represents dependence of the photoelectric section on the ray energy E, $f_{KN}(E)$ describes the relationship between the Compton section and the photon energy, $D_H(E)$ represents the energy spectrum of the X rays detected by the high-energy detectors, $D_L(E)$ represents the energy spectrum of the X rays detected by the low-energy detectors, $a_1$ represents photoelectric coefficient, $a_2$ represents Compton coefficient, $A_1$ represents photoelectric coefficient integral, and $A_2$ represents Compton coefficient integral. The integral is represented by the formula (4):

$$A = \int a \, dl \quad (4)$$

Then a linear equation system is established as:

$$A = \Sigma a \cdot l \quad (5)$$

More specifically, $a_1$ and $a_2$ are computed with the following systems of equations (6) and (7):

$$\begin{bmatrix} l_1(1) & l_2(1) & \cdots & \cdots & l_N(1) \\ l_1(2) & \ddots & & & \vdots \\ \vdots & & \ddots & & \vdots \\ \vdots & & & \ddots & \vdots \\ l_1(M) & \cdots & \cdots & \cdots & l_N(M) \end{bmatrix} \begin{bmatrix} a_{1,1} \\ a_{1,2} \\ \vdots \\ \vdots \\ a_{1,N} \end{bmatrix} = \begin{bmatrix} A_1(1) \\ A_1(2) \\ \vdots \\ \vdots \\ A_1(M) \end{bmatrix} \quad (6)$$

$$\begin{bmatrix} l_1(1) & l_2(1) & \cdots & \cdots & l_N(1) \\ l_1(2) & \ddots & & & \vdots \\ \vdots & & \ddots & & \vdots \\ \vdots & & & \ddots & \vdots \\ l_1(M) & \cdots & \cdots & \cdots & l_N(M) \end{bmatrix} \begin{bmatrix} a_{2,1} \\ a_{2,2} \\ \vdots \\ \vdots \\ a_{2,N} \end{bmatrix} = \begin{bmatrix} A_2(1) \\ A_2(2) \\ \vdots \\ \vdots \\ A_2(M) \end{bmatrix} \quad (7)$$

At step S15, the systems of equations established at step S14 are solved by the least square method to obtain the solution of a, i.e., photoelectric coefficient $a_1$, and Compton coefficient $a_2$. Then, at step S16, atomic number and electron density are computed with the formulas (8) and (9):

$$a_1 \approx K_1 \frac{N_A}{2} \rho Z^n (n \approx 3) \quad (8)$$

$$a_2 \approx K_2 \frac{N_A}{2} \rho \quad (9)$$

wherein Z represents atomic number, $\rho$ represents electron density, $N_A$ represents Avogadro constant, $K_1$ is a constant including all other coefficients independent from ray energy and material parameter, $K_2$ is also a constant including all other coefficients independent from ray energy and material parameter. Accordingly, the atomic number and the electron density of material in each of the divided region can be computed, and the material can be effectively identified. For example, a lookup table or a classification curve can be used to identify the material in each of the regions with the computed atomic number. Alternatively, both of the computed atomic number and electron density may be used to identify the material.

The method and system according to the embodiments of the present invention provide CT-image-based dual-energy material identification of low cost, small dose and fast scanning speed, by using only a few samples of dual-energy projections. The method and system are applicable in various fields like security inspection, lossless detection and medical treatment.

The foregoing description is only made to the embodiments of the present invention. It should be noted to those ordinarily skilled in the art that various modifications and refinements can be made within the principle of the present invention and should be encompassed by the scope of the present invention. The scope of the present invention is defined by the appended claims.

What is claimed is:

1. A dual-energy material identification method with under-sampling, comprising steps of:
   CT scanning an object under inspection with ray beams at a first energy level to obtain projection data at respective angles at the first energy level, and reconstructing a CT image of the object;
   CT scanning the object with ray beams at a second energy level to obtain projection data at a part of the respective angles at the second energy level;
   combining the projection data at the first and second energy levels to obtain dual-energy under-sampled data at the part of the respective angles;
   acquiring a photoelectric coefficient integral value and a Compton coefficient integral value from the dual-energy under-sampled data;
   segmenting the CT image of the object into a plurality of regions and computing a length by which the dual-energy rays cross each of the regions;
   computing the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;
   computing at least atomic number of material in each of the regions based on the photoelectric coefficient and the Compton coefficient; and
   identifying the material of the object based on at least the atomic number.

2. The method of claim 1, wherein the step of computing at least atomic number comprises computing the atomic number and the electron density of the material in each region, and the step of identifying comprises identifying the material of the object based on the atomic number and the electron density.

3. The method of claim 1, wherein the step of identifying comprises determining the material of the object in each of the regions by using a lookup table.

4. The method of claim 1, wherein the step of identifying comprises determining the material of the object in each of the regions by using a pre-established classification curve.

5. The method of claim 1, wherein projection data at a part of the respective angles at the second energy level comprise projection data at a single angle at the second energy level.

6. The method of claim 1, wherein projection data at a part of the respective angles at the second energy level comprise projection data at several angles at the second energy level, and correlation among the projection data at the several angles is less than a predefined threshold value.

7. The method of claim 1, further comprising a step of labeling the segmented regions.

8. A dual-energy material identification system with under-sampling, comprising:
   a ray generating device configured to generate ray beams at a first energy level and ray beams at a second energy level, the ray beams being intended to penetrate through an object under inspection;
   a mechanic rotation control section comprising a rotation device and a control system and configured to perform a rotatory scanning on the object;
   a data collecting subsystem comprising an one tier of array of detectors and configured to acquire transmission projection data for the ray beams penetrating through the object;
   a master control and data processing computer configured to control the ray generating device, the mechanic rotation control section and the data collecting subsystem to CT scan the object with ray beams at a first energy level to obtain projection data at respective angles at the first energy level, reconstruct a CT image of the object and CT scan the object with ray beams at a second energy level to obtain projection data at a part of the respective angles at the second energy level;
   wherein the master control and data processing computer is configured to:

combine the projection data at the first and second energy levels to obtain dual-energy under-sampled data at the part of the respective angles;

acquire a photoelectric coefficient integral value and a Compton coefficient integral value from the dual-energy under-sampled data;

segment the CT image of the object to obtain a plurality of segmented regions, and compute a length by which the dual-energy rays cross each of the regions;

compute the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

compute at least atomic number of material in each of the regions based on the photoelectric coefficient and the Compton coefficient; and identify the material of the object based on at least the atomic number.

9. The system of claim 8, wherein the master control and data processing computer is further configured to compute the atomic number and the electron density of the material in each region, and identify the material comprises a unit configured to identify the material of the object based on the atomic number and the electron density.

10. The system of claim 8, wherein the master control and data processing computer is further configured to determine the material of the object in each of the regions by using a lookup table.

11. The system of claim 8, wherein the master control and data processing computer is further configured to determine the material of the object in each of the regions by using a pre-established classification graph.

12. The system of claim 8, wherein projection data at a part of the respective angles at the second energy level comprise projection data at a single angle at the second energy level.

13. The system of claim 8, wherein projection data at a part of the respective angles at the second energy level comprise projection data at several angles at the second energy level, and correlation among the projection data at the several angles is less then a predefined threshold value.

14. The system of claim 8, wherein the master control and data processing computer is further configured to label the segmented regions.

* * * * *

UNITED STATES PATENT AND TRADEMARK OFFICE
CERTIFICATE OF CORRECTION

PATENT NO. : 8,582,857 B2 Page 1 of 1
APPLICATION NO. : 13/322243
DATED : November 12, 2013
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Twenty-second Day of September, 2015

Michelle K. Lee
*Director of the United States Patent and Trademark Office*